United States Patent
Bekemeier et al.

(10) Patent No.: US 8,980,959 B2
(45) Date of Patent: Mar. 17, 2015

(54) BI-MODAL EMULSIONS

(75) Inventors: Thomas Daniel Bekemeier, Birch Run, MI (US); Bethany Johnson, Midland, MI (US); Donald Taylor Liles, Midland, MI (US); Heidi Vandort, Sandord, MI (US); Brett Lee Zimmerman, Frankenmuth, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 14/002,366

(22) PCT Filed: Mar. 2, 2012

(86) PCT No.: PCT/US2012/027448
§ 371 (c)(1),
(2), (4) Date: Aug. 30, 2013

(87) PCT Pub. No.: WO2012/119062
PCT Pub. Date: Sep. 7, 2012

(65) Prior Publication Data
US 2013/0345342 A1    Dec. 26, 2013

Related U.S. Application Data

(60) Provisional application No. 61/448,849, filed on Mar. 3, 2011.

(51) Int. Cl.
| | | |
|---|---|---|
| B01F 3/08 | (2006.01) | |
| C08J 3/00 | (2006.01) | |
| C09D 5/02 | (2006.01) | |
| C08J 3/03 | (2006.01) | |
| C08L 83/04 | (2006.01) | |
| A61Q 19/00 | (2006.01) | |
| A61K 8/891 | (2006.01) | |
| A61K 8/06 | (2006.01) | |
| C08G 77/16 | (2006.01) | |

(52) U.S. Cl.
CPC . *C09D 5/022* (2013.01); *C08J 3/03* (2013.01); *C08L 83/04* (2013.01); *A61Q 19/00* (2013.01); *A61K 8/891* (2013.01); *A61K 8/062* (2013.01); *C08G 77/16* (2013.01); *C08J 2383/04* (2013.01); *C08L 2205/02* (2013.01); *A61K 2800/33* (2013.01)
USPC ............... 516/54; 516/53; 516/58; 516/65; 516/67; 516/76

(58) Field of Classification Search
None
See application file for complete search history.

(56) References Cited

U.S. PATENT DOCUMENTS

| | | | |
|---|---|---|---|
| 2,823,218 A | 2/1958 | Speier et al. | |
| 2,891,920 A | 6/1959 | Hyde et al. | |
| 3,294,725 A | 12/1966 | Findlay et al. | |
| 3,419,593 A | 12/1968 | Willing | |
| 3,715,334 A | 2/1973 | Karstedt | |
| 3,814,730 A | 6/1974 | Karstedt | |
| 3,923,705 A | 12/1975 | Smith | |
| 4,618,645 A | 10/1986 | Bauman et al. | |
| 4,824,877 A | 4/1989 | Glover et al. | |
| 4,874,547 A | 10/1989 | Narula | |
| 5,175,325 A | 12/1992 | Brown et al. | |
| 5,661,215 A | 8/1997 | Gee et al. | |
| 5,817,714 A | 10/1998 | Gravier et al. | |
| 6,248,855 B1 | 6/2001 | Dalle et al. | |
| 6,316,541 B1 | 11/2001 | Gee | |
| 6,395,790 B1 | 5/2002 | Creutz et al. | |
| 8,729,157 B2 * | 5/2014 | Lin | ................. 523/336 |
| 2002/0108721 A1 | 8/2002 | Wrolson et al. | |
| 2004/0063818 A1 | 4/2004 | Silber et al. | |
| 2004/0138373 A1 | 7/2004 | Hamachi et al. | |

FOREIGN PATENT DOCUMENTS

| | | |
|---|---|---|
| EP | 0200009 A2 | 11/1986 |
| EP | 1132417 A2 | 9/2001 |
| WO | WO 9514728 A1 | 6/1995 |
| WO | WO 2007117720 A2 | 10/2007 |
| WO | WO 2009128883 A1 | 10/2009 |
| WO | 2009148902 | 12/2009 |
| WO | WO 2009/148902 A1 | 12/2009 |
| WO | WO 2012119068 A2 | 9/2012 |

OTHER PUBLICATIONS

English language abstract for EP 1132417 extracted from espacenet.com database Feb. 20, 2014, 11 pages.
International Search Report for Application No. PCT/US2012/027448 dated Sep. 11, 2012, 3 pages.
International Search Report for Application No. PCT/US2012/027457 dated Sep. 11, 2012, 3 pages.

\* cited by examiner

*Primary Examiner* — Marc Zimmer
(74) *Attorney, Agent, or Firm* — Baltazar Gomez

(57) ABSTRACT

A process for preparing bi-modal water emulsions is disclosed comprising: I) forming a mixture comprising; A) 100 parts by weight of a hydrophobic oil, B) 1 to 1000 part by weight of a water continuous emulsion having at least one surfactant, II) admixing additional quantities of the water continuous emulsion and/or water to the mixture from step I) to form a bi-modal emulsion.

16 Claims, No Drawings

BI-MODAL EMULSIONS

CROSS-REFERENCE TO RELATED APPLICATIONS

This application is the National Stage of International Patent Application No. PCT/US2012/027448, filed on Mar. 2, 2012, which claims priority to and all the advantages of U.S. Application No. 61/448,849, filed on Mar. 3, 2011, the content of which is incorporated herein by reference.

BACKGROUND OF THE INVENTION

While numerous advancements have been made in the emulsions field, there are several long standing needs that remain. For example, as the percent solids of an emulsion increases, in most emulsions the viscosity also increases. Emulsions having a solids level greater than 75 weight % can become so viscous that they are non-pourable. This effectively renders such emulsion products unusable in many applications due to the handling difficulties of such viscous compositions.

Another long standing need in this field is to stabilize emulsions with a minimal amount of surfactants. This is a particular need when the emulsions are used to form coatings, such as protective architectural coatings. Residual surfactant on coatings formed from emulsions can have several detrimental effects on the physical property profile of the coatings such as decreased hydrophobicity and/or poorer dirt resistance. The use of emulsions with minimal amount of surfactants is also highly desirable for application in personal care products, especially for skin and cosmetic formulations where residual surfactants may cause skin irritation.

Reducing the presence of solvents, un-reacted siloxanes, catalyst residues, cyclic polymerization byproducts, and other impurities in silicone emulsions is an ongoing challenge in the art. The need to reduce such impurities may arise, among other reasons, when such impurities are incompatible with downstream applications (for example, medical, cosmetic, and personal care applications), where the presence of such impurities would reduce the stability of an emulsion, or where regulatory requirements require removal or reduction of their presence. In particular, there is an interest to reduce the presence of cyclosiloxanes, such as octamethylcyclotetrasiloxanes and decamethylcyclopentasiloxanes, in silicone emulsions.

Thus, a need exists to identify a process that provides emulsion products having high solids contents that remain pourable. A further need exists to reduce the concentration of surfactants in emulsion products, especially at high solid content emulsions. Yet, a further need exists to provide silicone emulsions having reduced content of cyclosiloxane concentrations.

BRIEF SUMMARY OF THE INVENTION

The present inventors have discovered a process that provides high solids content emulsions having lower viscosities than emulsions of similar solids content prepared by other methods. The present disclosure relates to a process for preparing bi-modal water emulsions, that is, water continuous emulsions containing at least two distinct dispersed phases. The present disclosure provides a process for making a bi-modal water continuous emulsion comprising:
  I) forming a mixture comprising;
  A) 100 parts by weight of a hydrophobic oil,
  B) 1 to 1000 part by weight of a water continuous emulsion having at least one surfactant,
  II) admixing additional quantities of the water continuous emulsion and/or water to the mixture from step I) to form a bi-modal emulsion.

The inventors believe the present process is advantageous due to its versatility to prepare a wide range of bi-modal emulsions having high solids content. The disclosed process may be used to prepare a variety of bi-modal emulsions having two distinct dispersed phases. Each distinct phase may contain either organic or silicone oil.

DETAILED DESCRIPTION OF THE INVENTION

The present disclosure provides a process for making a bi-modal water continuous emulsion comprising:
  I) forming a mixture comprising;
  A) 100 parts by weight of a hydrophobic oil,
  B) 1 to 1000 part by weight of a water continuous emulsion having at least one surfactant,
  II) admixing additional quantities of the water continuous emulsion and/or water to the mixture from step I) to form a bi-modal emulsion.

The present process provides bi-modal emulsions. The bi-modal emulsions are water continuous emulsions having two distinct dispersed phases. As used herein, "dispersed phase" refers to the water insoluble particles suspended in the continuous aqueous phase of the emulsion. The first dispersed phase contains a hydrophobic oil while the independent second dispersed phase also contains a hydrophobic oil, which may be the same or different from the hydrophobic oil in the first dispersed phase. Each dispersed phase may be characterized by its own average particle size distribution in the emulsion, in other words, the average particle size of the two independent dispersed phases demonstrate a "bi-modal" distribution.

The first step in the present process is to form a mixture comprising of, consisting essentially of, or consisting of;
  A) 100 parts by weight of a hydrophobic oil,
  B) 1 to 1000 parts by weight of a water continuous emulsion having at least one surfactant.

A) The Hydrophobic Oil

Component A) of the present emulsions contains a hydrophobic oil. The hydrophobic oil may be selected from an a) an organic oil, b) a silicone, or combinations thereof.

The hydrophobic oil may be selected from various organic compounds or organic polymers. In this embodiment, the hydrophobic oil phase is considered to be an organic oil phase, which means the majority of this dispersed phase comprises organic compounds or organic polymers. The organic oil may be selected from hydrocarbons, oils derived from natural fats or oils, organic polymers, or mixtures thereof.

Suitable organic oil components include, but are not limited to, natural oils such as coconut oil; hydrocarbons such as mineral oil and hydrogenated polyisobutene; fatty alcohols such as octyldodecanol; esters such as C12-C15 alkyl benzoate; diesters such as propylene dipelarganate; and triesters, such as glyceryl trioctanoate.

The organic oil composition may be selected from esters having the structure RCO—OR' wherein RCO represents the carboxylic acid radical and wherein OR' is an alcohol residue. Examples of these ester organic oils include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, cocodicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or mixtures of octyldodecanol, acetylated lanolin alcohol, cetyl acetate, isododecanol, polyglyceryl-3-diisostearate, or mixtures thereof.

Suitable natural oils include castor oil, lanolin and lanolin derivatives, triisocetyl citrate, sorbitan sesquioleate, C10-18 triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, castor oil, illipe butter, rapeseed oil, soybean oil, sunflower seed oil, pine oil, tallow, tricaprin, trihydroxystearin, triisostearin, trilaurin, trilinolein, trimyristin, triolein, tripalmitin, tristearin, walnut oil, wheat germ oil, cholesterol, or mixtures thereof.

In one embodiment, the organic oil contains an organic polymer such as polybutenes or polyisobutylenes, polyacrylates, polystyrenes, polybutadienes, polyamides, polyesters, polyacrylates, polyurethanes, polysulfones, polysulfides, as well as copolymers or terpolymers containing these organic polymers, and mixtures of any of these. Representative, non-limiting examples of organic polymers suitable for use as component A) in the present process include the polybutenes sold by INEOS Oligomers under the trademarked names Indopol® and Panalane®. (INEOS Oligomers, League City, Tex.).

The hydrophobic oil may be selected from various silicone polymers. In this embodiment, the hydrophobic oil phase is considered to be a silicone oil phase, which means the majority of this dispersed phase comprises silicone polymers. As used herein, "silicone" refers to a composition containing at least one organopolysiloxane. Organopolysiloxanes are polymers containing siloxy units independently selected from $(R_3SiO_{1/2})$, $(R_2SiO_{2/2})$, $(RSiO_{3/2})$, or $(SiO_{4/2})$ siloxy units, where R may be any organic group, alternatively R is a hydrocarbon group containing 1 to 30 carbons, alternatively R is an alkyl group containing 1 to 12 carbon atoms, or alternatively R is methyl or phenyl. These siloxy units are commonly referred to as M, D, T, and Q units respectively. Their molecular structures are listed below:

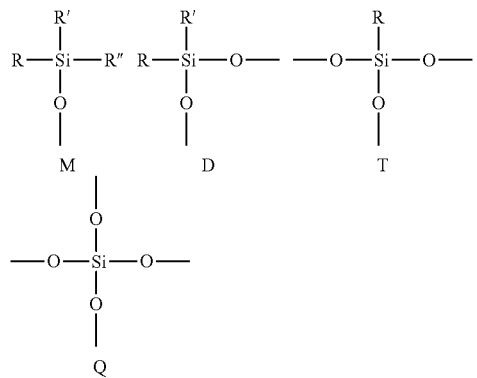

These siloxy units can be combined in various manners to form cyclic, linear, or branched structures. The chemical and physical properties of the resulting polymeric structures vary depending on the number and type of siloxy units in the organopolysiloxane.

The silicone composition may contain a single organopolysiloxane, or mixture of various organopolysiloxanes. The silicone composition may contain silicone fluids, silicone gums, silicone rubbers, silicone elastomers, silicone resins, or any combinations thereof.

In one embodiment the organopolysiloxane is selected from a polydimethylsiloxane. The polydimethylsiloxane may be a trimethoxy or hydroxy (SiOH) terminated polydimethylsiloxane. Trimethoxy end blocked polydimethysiloxanes have the formula $Me_3SiO(Me_2SiO_{2/2})_{dp}SiMe_3$ wherein the degree of polymerization (dp) is greater than 1, or alternatively the dp is sufficient to provide a kinematic viscosity that may range from 1 to 1,000,000 mm$^2$/s at 25° C., or alternatively from 100 to 600,000 mm$^2$/s at 25° C., or alternatively from 1000 to 600,000 mm$^2$/s at 25° C. Representative commercial polydimethylsiloxanes include Dow Corning 200 Fluids®, (Dow Corning Corporation, Midland Mich.) available in varying viscosities from 1 to 600,000 mm$^2$/s at 25° C.

In another embodiment the silicone composition contains a mixture of organopolysiloxanes that can react with each other to form higher molecular weight organopolysiloxanes. The reaction to form higher molecular weight organopolysiloxanes may be effected by condensation or hydrosilylation of the organopolysiloxanes.

In one embodiment the silicone composition contains organopolysiloxanes components that can react via hydrosilylation. In this embodiment, the silicone component contains;

b$^1$) an organopolysiloxane having at least two silicon-bonded alkenyl groups per molecule, b$^2$) an organohydrogensiloxane having at least two SiH groups per molecule, and b$^3$) a hydrosilylation catalyst, The organopolysiloxane having at least two silicon-bonded alkenyl groups per molecule comprises at least two siloxy units represented by the formula $R^2R_mSiO_{(4-m)/2}$ wherein R is an hydrocarbon group containing 1 to 30 carbon atoms, $R^2$ is an alkenyl group containing 2 to 12 carbon atoms, and m is zero to 2. The $R^2$ alkenyl groups of Component b$^1$) are exemplified by vinyl, allyl, 3-butenyl, 4-pentenyl, 5-hexenyl, 6-heptenyl, 7-octenyl, 8-nonenyl, 9-decenyl, 10-undecenyl, 4,7-octadienyl, 5,8-nonadienyl, 5,9-decadienyl, 6,11-dodecadienyl and 4,8-nonadienyl.

The $R^2$ alkenyl group may be present on any mono, di, or tri siloxy unit in the organopolysiloxane, for example; $(R^2R_2SiO_{1/2})$, $(R^2RSiO_{2/2})$, or $(R^2SiO_{3/2})$; as well as in combination with other siloxy units not containing an $R^2$ substituent, such as $(R_3SiO_{1/2})$, $(R_2SiO_{2/2})$, $(RSiO_{3/2})$, or $(SiO_{4/2})$ siloxy units where R is a hydrocarbon containing 1 to 20 carbons, alternatively an alkyl group containing 1 to 12 carbons, alternatively an alkyl group containing 1 to 6 carbons or alternatively methyl; providing there are at least two $R^2$ substituents in the organopolysiloxane. The monovalent hydrocarbon group R having from 1 to 20 carbon atoms is exemplified by alkyl groups such as: methyl, ethyl, propyl, butyl, hexyl, octyl, and decyl; cycloaliphatic groups such as cyclohexyl; aryl groups such as phenyl, tolyl, and xylyl; and aralkyl groups such as benzyl and phenylethyl.

Component b$^1$) may be selected from trimethylsiloxy-terminated polydimethylsiloxane-polymethylvinylsiloxane copolymers, vinyldimethylsiloxy-terminated polydimethylsiloxane-polymethylvinylsiloxane copolymers, trimethylsiloxy-terminated polydimethylsiloxane-polymethylhexenylsiloxane copolymers, hexenyldimethylsiloxy-terminated polydimethylsiloxane-polymethylhexenylsiloxane copolymers, trimethylsiloxy-terminated polymethylvinylsiloxane polymers, trimethylsiloxy-terminated polymethylhexenylsiloxane polymers, vinyldimethylsiloxy-terminated polydimethylsiloxane polymers, hexenyldimethylsiloxy-terminated polydimethylsiloxane polymers, or any combination thereof, each having a degree of polymerization of from 10 to 300, or alternatively having a viscosity at 25° C. of 10 to 1000 mPa·s.

Component $b^2$) is an organohydrogensiloxane having an average of greater than two silicon bonded hydrogen atoms per molecule. As used herein, an organohydrogensiloxane is any organopolysiloxane containing a silicon-bonded hydrogen atom (SiH).

Organohydrogensiloxanes are organopolysiloxanes having at least one SiH containing siloxy unit, that is at least one siloxy unit in the organopolysiloxane has the formula $(R_2HSiO_{1/2})$, $(RHSiO_{2/2})$, or $(HSiO_{3/2})$. Thus, the organohydrogensiloxanes useful in the present invention may comprise any number of $(R_3SiO_{1/2})$, $(R_2SiO_{2/2})$, $(RSiO_{3/2})$, $(R_2HSiO_{1/2})$, $(RHSiO_{2/2})$, $(HSiO_{3/2})$ or $(SiO_{4/2})$ siloxy units, providing there are on average at least two SiH siloxy units in the molecule. Component $b^2$) can be a single linear or branched organohydrogensiloxane or a combination comprising two or more linear or branched organohydrogensiloxanes that differ in at least one of the following properties; structure, viscosity, average molecular weight, siloxane units, and sequence. There are no particular restrictions on the molecular weight of the organohydrogensiloxane, but typically the viscosity of the organohydrogensiloxane at 25° C. is from 3 to 10,000 mPa·s, alternatively 3 to 1,000 mPa·s, or alternatively 10 to 500 mPa·s.

The amount of SiH units present in the organohydrogensiloxane may vary, providing there are at least two SiH units per organohydrogensiloxane molecule. The amount of SiH units present in the organohydrogensiloxane is expressed herein as % SiH which is the weight percent of hydrogen in the organohydrogensiloxane. Typically, the % SiH varies from 0.01 to 10%, alternatively from 0.1 to 5%, or alternatively from 0.5 to 2%.

The organohydrogensiloxane may comprise the average formula;

$(R^3_3SiO_{1/2})_a(R^4_2SiO_{2/2})_b(R^4HSiO_{2/2})_c$ wherein
$R^3$ is hydrogen or $R^4$,
$R^4$ is a monovalent hydrocarbon group having from 1 to 10 carbon atoms
a≥2,
b≥0, alternatively b=1 to 500, alternatively b=1 to 200,
c≥2, alternatively c=2 to 200, alternatively c=2 to 100.

$R^4$ may be a substituted or unsubstituted aliphatic or aromatic hydrocarbyl. Monovalent unsubstituted aliphatic hydrocarbyls are exemplified by, but not limited to alkyl groups such as methyl, ethyl, propyl, pentyl, octyl, undecyl, and octadecyl and cycloalkyl groups such as cyclohexyl. Monovalent substituted aliphatic hydrocarbyls are exemplified by, but not limited to halogenated alkyl groups such as chloromethyl, 3-chloropropyl, and 3,3,3-trifluoropropyl. The aromatic hydrocarbon group is exemplified by, but not limited to, phenyl, tolyl, xylyl, benzyl, styryl, and 2-phenylethyl.

The amounts of components $b^1$) and $b^2$) used may vary, but typically the amounts of components $b^1$) and $b^2$) are selected so as to provide a molar ratio of the alkenyl groups to SiH in the composition that is greater than 1.

Component $b^3$) is a hydrosilylation catalyst. The hydrosilylation catalyst may be any suitable Group VIII metal based catalyst selected from a platinum, rhodium, iridium, palladium or ruthenium. Group VIII group metal containing catalysts useful to catalyze curing of the present compositions can be any of those known to catalyze reactions of silicon bonded hydrogen atoms with silicon bonded unsaturated hydrocarbon groups. The preferred Group VIII metal for use as a catalyst to effect cure of the present compositions by hydrosilylation is a platinum based catalyst. Some preferred platinum based hydrosilylation catalysts for curing the present composition are platinum metal, platinum compounds and platinum complexes. Suitable platinum catalysts are described in U.S. Pat. No. 2,823,218 (commonly referred to as "Speier's catalyst) and U.S. Pat. No. 3,923,705. The platinum catalyst may be "Karstedt's catalyst", which is described in Karstedt's U.S. Pat. Nos. 3,715,334 and 3,814,730. Karstedt's catalyst is a platinum divinyl tetramethyl disiloxane complex typically containing about one-weight percent of platinum in a solvent such as toluene. Alternatively the platinum catalyst may be a reaction product of chloroplatinic acid and an organosilicon compound containing terminal aliphatic unsaturation, as described in U.S. Pat. No. 3,419,593. Alternatively, the hydrosilylation catalyst is a neutralized complex of platinum chloride and divinyl tetramethyl disiloxane, as described in U.S. Pat. No. 5,175,325.

The amounts of catalyst $b^3$) used may vary, but typically an amount is used to effect the hydrosilylation reaction. When the catalyst is a Pt compound, typically a sufficient amount of the compound is added to provide 2 to 500 ppm of Pt in the silicone composition.

Additional components may be added to the hydrosilylation reaction. For example, heptamethyltrisiloxysilane may be added as an endblocker to control molecular weight of the organopolysiloxane product.

In one embodiment the silicone composition contains organopolysiloxanes components that can react via condensation. In this embodiment, the silicone composition contains an organopolysiloxane having at least two siloxy units with a substituent capable of reacting via condensation. Suitable substitutes on the siloxy units of the organopolysiloxanes include silanol, alkoxy, acetoxy, oxime functional groups. In this embodiment, the silicone composition will further contain a catalyst known in the art for enhancing condensation cure of organopolysiloxanes such as a tin or titanium catalyst. In a further embodiment, the organopolysiloxane is a silanol endblocked polydimethylsiloxane having a kinematic viscosity that may range from 1 to 100,000 mm²/s at 25° C., or alternatively from 1 to 10,000 mm²/s at 25° C. Representative commercial silanol endblocked polydimethylsiloxanes include; XIAMETER® OHX-4000 2000cs, XIAMETER® OHX-4010 4000cs, XIAMETER® OHX-4012 6000cs, XIAMETER® OHX-4040 14000cs, XIAMETER® PMX-0930 Silanol fluid, DOW CORNING® 3-0133 Polymer, DOW CORNING® 3-0213 Polymer, DOW CORNING® 3-0113 Polymer, DOW CORNING® 3-0084 Polymer, and DOW CORNING® 2-1273 Fluid.

In one embodiment the silicone composition contains organopolysiloxanes having at least one siloxy unit substituted with an organofunctional group. The organofunctional organopolysiloxanes useful in the present process are characterized by having at least one of the R groups in the formula $R_nSiO_{(4-n)/2}$ be an organofunctional group. Representative non-limiting organofunctional groups include; amino, amido, epoxy, mercapto, polyether (polyoxyalkylene) groups, and any mixture thereof. The organofunctional group may be present on any siloxy unit having an R substituent, that is, they may be present on any $(R_3SiO_{0.5})$, $(R_2SiO)$, or $(RSiO_{1.5})$ unit.

In a further embodiment, the organofunctional group is an amino group. Amino-functional groups may be designated in the formulas herein as $R^N$ and is illustrated by groups having the formula; 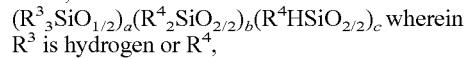 —$R^1NHR^2$, —$R^1NR^2_2$, or —$R^1NHR^1NHR^2$, wherein each $R^1$ is independently a divalent hydrocarbon group having at least 2 carbon atoms, and $R^2$ is hydrogen or an alkyl group. Each $R^1$ is typically an alkylene group having from 2 to 20 carbon atoms. Some examples of suitable amino-functional hydrocarbon groups are; —$CH_2CH_2NH_2$,

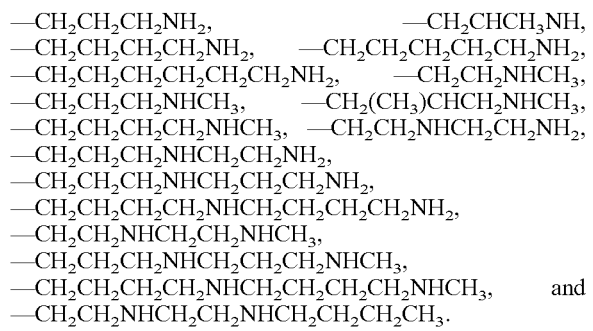

Representative commercial aminofunctional organopolysiloxanes include; XIAMETER® OFX-8040 Fluid, XIAMETER® OHX-8600 Fluid, XIAMETER® OHX-8630 Fluid, XIAMETER® OHX-8803 Fluid, DOW CORNING® AP-8087 Fluid, DOW CORNING® 2-8040 Polymer, DOW CORNING® 8566 Polymer, DOW CORNING® 8600 HYDROPHILIC SOFTENER, and DOW CORNING® 8803 Polymer.

B) The Water Continuous Emulsion

Component B) in the present process is a water continuous emulsion. Component B) may be a single water continuous emulsion, or a combination of water continuous emulsions.

The water continuous emulsion(s) useful as component B) in the present process contains at least one surfactant. The surfactant may vary, but typically is chosen from those surfactants that enhance the formation of water continuous emulsions. The surfactant may be an anionic surfactant, cationic surfactant, nonionic surfactant, amphoteric surfactant, or a mixture of any of these surfactants.

Representative examples of suitable anionic surfactants include alkali metal, amine, or ammonium salts of higher fatty acids, alkylaryl sulphonates such as sodium dodecyl benzene sulfonate, long chain fatty alcohol sulfates, olefin sulfates and olefin sulfonates, sulfated monoglycerides, sulfated esters, sulfonated ethoxylated alcohols, sulfosuccinates, alkane sulfonates, phosphate esters, alkyl isethionates, alkyl taurates, and alkyl sarcosinates.

Representative examples of suitable cationic surfactants include alkylamine salts, quaternary ammonium salts, sulphonium salts, and phosphonium salts. Representative examples of suitable nonionic surfactants include condensates of ethylene oxide with long chain fatty alcohols or fatty acids such as a $C_{12-16}$ alcohol, condensates of ethylene oxide with an amine or an amide, condensation products of ethylene and propylene oxide, esters of glycerol, sucrose, sorbitol, fatty acid alkylol amides, sucrose esters, fluoro-surfactants, and fatty amine oxides. Representative examples of suitable amphoteric surfactants include imidazoline compounds, alkylaminoacid salts, and betaines.

Representative examples of suitable commercially available nonionic surfactants include polyoxyethylene fatty alcohols sold under the tradename BRIJ® by Croda (ICI Surfactants), Wilmington, Del. Some examples are BRIJ® 35 Liquid, an ethoxylated alcohol known as polyoxyethylene (23) lauryl ether, and BRIJ® 30, another ethoxylated alcohol known as polyoxyethylene (4) lauryl ether. Some additional nonionic surfactants include ethoxylated alcohols sold under the trademark TERGITOL® by The Dow Chemical Company, Midland, Mich. Some example are TERGITOL® TMN-6, an ethoxylated alcohol known as ethoxylated trimethylnonanol; and various of the ethoxylated alcohols, i.e., $C_{12}$-$C_{14}$ secondary alcohol ethoxylates, sold under the trademarks TERGITOL® 15-S-5, TERGITOL® 15-S-12, TERGITOL® 15-S-15, and TERGITOL® 15-S-40. Lutensol supplied by BASF in the series of Lutensol XP known as ethoxylated, C10-Guerbet alcohol and Lutensol TO known as ethoxylated, iso-C13 alcohol may also be used.

When mixtures containing nonionic surfactants are used, one nonionic surfactant may have a low Hydrophile-Lipophile Balance (HLB) and the other nonionic surfactant may have a high HLB, such that the two nonionic surfactants have a combined HLB of 11-15, alternatively a combined HLB of 12.5-14.5.

The water continuous emulsion may be selected from those considered in the art to be a "macro" or "micro" emulsion. In other words, the average particle size of the water continuous emulsion may vary from 0.001 to 1000 μm, alternatively from 0.01 to 20 μm, or alternatively from 0.02 to 10 μm.

In one specific embodiment, the water continuous emulsion is a microemulsion having an average particle size of less than 100 nm.

In one embodiment, the water continuous emulsion may be selected from a "mechanical emulsion". As used herein, mechanical emulsions refer to those emulsion in the art produced by using mechanical energy (such as from high shearing forces). The mechanical emulsions may be either organic or silicone.

In one embodiment, the water continuous emulsion may be considered an "emulsion polymer", in other words, an emulsion formed by emulsion polymerization techniques. The emulsion polymer may be either organic or silicone.

In a further embodiment, the organic emulsion may be selected from those emulsions considered in the art to be a "latex". A latex is a stable emulsion of a polymer or mixture of polymers, which may be either natural or synthetic. The latex may be organic or silicone.

In one embodiment, the water continuous emulsion is an organic emulsion. In this embodiment, the dispersed phase in the emulsion contains at least one organic oil, such as those described above as component A).

In a further embodiment, the organic emulsion may be selected from a latex. Representative, non-limiting suitable synthetic organic lattices include; styrene, styrene-butadiene, acrylonitrile, acrylonitrile-butadiene, acrylics, polyvinyl acetate, polyacrylate, polyurethane, epoxy, and alkyds. Representative, non-limiting examples of commercially available lattices useful as the water continuous emulsion in the present process include the series of lattices sold by BASF under the tradename of Joncryl®, such as Joncryl® 77 (BASF).

In another embodiment, the organic emulsion is an emulsion of a natural oil, such as pine oil. A representative, non-limiting example of commercially available natural oil emulsions useful as the water continuous emulsion in the present process includes Pinesol®. The organic emulsion may also be an emulsion of a wax, such as Michem® Wax Emulsion. The organic emulsion may also be a PTFE dispersion.

In one embodiment, the water continuous emulsion is a silicone emulsion. In this embodiment, the dispersed phase in the emulsion contains at least one organopolysiloxane, such as the organopolysiloxanes as described above for use as component A).

In a further embodiment, the silicone emulsion is a mechanical emulsion. Representative, non-limiting suitable examples of suitable silicone emulsions produced by mechanical techniques are taught in U.S. Pat. No. 6,395,790, which is incorporated herein by reference.

In a further embodiment, the emulsion polymer is a silicone emulsion polymer. The silicone emulsion polymer. Representative, non-limiting suitable examples of suitable silicone emulsions produced by emulsion polymerization techniques suitable for use in the present process are taught in; U.S. Pat. No. 2,891,920, U.S. Pat. No. 3,294,725, U.S. Pat.

No. 5,661,215, U.S. Pat. No. 5,817,714, and U.S. Pat. No. 6,316,541, which are incorporated herein by reference. Representative, non-limiting commercial products suitable as silicone emulsions produced by emulsion polymerization techniques include; Dow Corning® HV-490, Dow Corning® 929, Dow Corning® 939, Dow Corning 949, Dow Corning 1391, Dow Corning 2-1865, Dow Corning® 2-1870, Dow Corning® 2-1938, DC 2-8194, and Dow Corning® 2-8194 (Dow Corning Corporation, Midland Mich.).

In one embodiment, the water continuous emulsion may be prepared using suspension polymerization techniques. The suspension emulsions may be either organic or silicone.

In a further embodiment, the water continuous emulsion prepared using suspension polymerization techniques is a silicone emulsion polymer. Representative, non-limiting examples of suitable silicone emulsions produced by suspension polymerization techniques suitable for use in the present process are taught in; U.S. Pat. No. 4,618,645, U.S. Pat. No. 6,248,855, and U.S. Pat. No. 6,395,790. Representative, non-limiting commercial products suitable as silicone emulsions produced by suspension polymerization techniques include; Dow Corning® 1997, Dow Corning® HMW 2220, Xiameter® MEM 1785 Emulsion, Dow Corning® 1788 Emulsion (Dow Corning Corporation, Midland Mich.).

Mixing in step (I) can be accomplished by any method known in the art to effect mixing of high viscosity materials. The mixing may occur either as a batch, semi-continuous, or continuous process. Mixing may occur, for example using, batch mixing equipments with medium/low shear include change-can mixers, double-planetary mixers, conical-screw mixers, ribbon blenders, double-arm or sigma-blade mixers; batch equipments with high-shear and high-speed dispersers include those made by Charles Ross & Sons (NY), Hockmeyer Equipment Corp. (NJ); batch equipments with high shear actions include Banbury-type (CW Brabender Instruments Inc., NJ) and Henschel type (Henschel mixers America, TX). Illustrative examples of continuous mixers/compounders include extruders single-screw, twin-screw, and multi-screw extruders, co-rotating extruders, such as those manufactured by Krupp Werner & Pfleiderer Corp (Ramsey, N.J.), and Leistritz (NJ); twin-screw counter-rotating extruders, two-stage extruders, twin-rotor continuous mixers, dynamic or static mixers or combinations of these equipments.

The temperature and pressure at which the mixing of step I occurs is not critical, but generally is conducted at ambient temperature and pressures. Typically, the temperature of the mixture will increase during the mixing process due to the mechanical energy associated when shearing such high viscosity materials.

Typically 1 to 1000 parts by weight of the water continuous emulsion are mixed for every 100 parts by weight of component A) in the step I mixture, alternatively from 5 to 500 parts per 100 parts by weight of component A) in the step I mixture, or alternatively from 5 to 100 parts per 100 parts by weight of component A) the step I mixture.

In one embodiment of the present process, step I involves forming a mixture consisting essentially of;
A) 100 parts by weight of a hydrophobic oil,
B) 1 to 1000 parts by weight of a water continuous emulsion having at least one surfactant. In this embodiment, the mixture formed in step I) is "essentially free" from any other surfactant compounds or components other than components A) and B). As used herein, "essentially free" means no other surfactant compounds are added to the mixture formed in step I), other than the surfactant(s) present in B) the water continuous emulsion.

Step II) of the process involves admixing additional quantities of the water continuous emulsion and/or water to the mixture from step I) to form a bi-modal emulsion.

The amount of the additional quantities of the water continuous emulsion and/or water used in step II) may vary depending on the selection of components A) and B). Typically the amount of additional water continuous emulsion and/or water admixed in step II) of the present process may vary from 1 to 1000 parts by weight of the step I mixture, alternatively from 5 to 500 parts per 100 parts by weight, or alternatively from 5 to 100 parts per 100 parts by weight.

In step II) of the present process, additional quantities of the water continuous emulsion may be used alone, or alternatively be combined with varying quantities of water. Alternatively, additional quantities of water may be added alone without any additional quantities of the water continuous emulsion. The selection of using additional quantities of the water continuous emulsion alone, in combination with varying amounts of water, or water alone will depend on the initial selection of the water continuous emulsion and the desired physical properties of the resulting bi-modal emulsion. For example, high solids bi-modal emulsions may be prepared with only the addition of the water continuous emulsion. Conversely, low solids bi-modal emulsions may require the addition of water as well.

The water continuous emulsion and/or water is added to the mixture from step I at such a rate, with additional mixing, so as to form an emulsion of the mixture of step I. The water continuous emulsion added to the mixture from step I may be done in incremental portions, whereby each incremental portion comprises less than 50 weight % of the mixture from step I, alternatively 25 weight % of the mixture from step I, and each incremental portion of water continuous emulsion is added successively to the previous after the dispersion of the previous incremental portion of water continuous emulsion, wherein sufficient incremental portions of water continuous emulsion are added to form the bi-modal emulsion.

The number of incremental portions of the water continuous emulsion and/or water added to the mixture from step I may vary, but typically at least 2, alternatively, at least 3 incremental portions are added.

Mixing in step (II) can be accomplished by any method known in the art to effect mixing of high viscosity materials and/or effect the formation of an emulsion. The mixing may occur either as a batch, semi-continuous, or continuous process. Any of the mixing methods as described for step (I), may be used to effect mixing in step (II). Alternatively, mixing in step (II) may also occur via those techniques known in the art to provide high shear mixing to effect formation of emulsions. Representative of such high shear mixing techniques include; high speed stirrers, homogenizers, Sonolators®, microfluidizers, Ross mixers, Eppenbach colloid mills, Flacktek Speedmixers, and other similar shear devices.

Optionally, the emulsion formed in step (II) may be further sheared according to step (III) to reduce particle size and/or improve long term storage stability. The shearing may occur by any of the mixing techniques discussed above.

The present invention further relates to the bi-modal water continuous emulsions obtained using the present process.

The water continuous emulsions prepared by the process of the present disclosure may be characterized by their bi-modal particle size distribution. The particle size may be determined by laser diffraction of the emulsion. Suitable laser diffraction techniques are well known in the art. The particle size is obtained from a particle size distribution (PSD). The PSD can be determined on a volume, surface, length basis. The volume particle size is equal to the diameter of the sphere that has the same volume as a given particle. The term Dv, as used herein, represents the average volume particle size of the dispersed particles. Dv 50 is the particle size measured in volume corresponding to 50% of the cumulative particle population. In other words if Dv 50=10 µm, 50% of the particle have an average volume particle size below 10 µm and 50% of the particle have a volume average particle size above 10 µm. Dv 90 is the particle size measured in volume corresponding to 90% of the cumulative particle population. Mode 1 is the median of the distribution of the first population of particles within a bimodal particle distribution and Mode 2 is the median of the second.

In some instances, it may be necessary to conduct two separate evaluations of particle size, especially when the particle sizes distributions of the resulting bi-modal emulsions exhibit a wide variation in size. In these instances a Malvern-Mastersizer® 2000 may be used to obtain particle size distributions in the range 0.5 to 1000 µm, while a Microtrac-Nanotrac® may be used to measure particle size distributions in the ranges less than 0.5 µm.

The average volume particle size of the dispersed particles in the oil/water emulsions is between 0.001 µm and 1000 µm; or between 0.01 µm and 20 µm; or between 0.02 µm and 10 µm.

Alternatively, the average volume particle size of each of the unique dispersed phases (that is the first dispersed phase, and the second dispersed phase), may be reported. The average volume particle size of the first dispersed particles in the oil/water emulsions is between 0.1 µm and 500 µm; or between 0.1 µm and 100 µm; or between 0.2 µm and 30 µm. The average volume particle size of the second dispersed particles in the oil/water emulsions is between 0.1 µm and 500 µm; or between 0.1 µm and 100 µm; or between 0.2 µm and 30 µm.

While not wishing to be bound by any theory, the present inventors believe particle size distribution of the second dispersed phase results from the emulsification of the hydrophobic oil, while particle size distribution of the first dispersed phase results from the particles originating from the water continuous emulsion used in the present process. However, there may be certain instances where the two overlap sufficiently that a bi-modal distribution is not observable using the particle size determination techniques described above.

The bimodal particle size distribution may also be observed using optical microscopy techniques.

In another embodiment, the bi-modal emulsions may be considered as a "high solids" emulsion, wherein the bi-modal emulsion contains at least 75% by weight of components A) and B), alternatively the bi-modal emulsion contains at least 80% by weight of components A) and B), alternatively the bi-modal emulsion contains at least 85% by weight of components A) and B), alternatively the bi-modal emulsion contains at least 90% by weight of components A) and B).

In a further embodiment, the "high solids" bi-modal emulsion remain pourable. Thus, the bi-modal emulsions may have a viscosity less than 600,000 cP, alternatively less than 200,000 cP, or alternatively less than 100,000 cP, as measured at 25° C.

In another embodiment, the total surfactant concentration in the bi-modal emulsion is less than 4.0 weight %, alternatively less than 1.0 weight %, or alternatively less than 0.2 weight %.

In another embodiment, the bi-modal silicone emulsions produced by the present process contains less than 1.0 weight % cyclosiloxanes, or alternatively containing less than 0.5 weight % cyclosiloxanes, or alternatively containing less than 0.1 weight % cyclosiloxanes.

The present bi-modal emulsions are useful a variety of applications where it is desirable to provide pourable water based organic or silicone materials having a high solids content. Such applications include various coating applications. The present emulsions may also be beneficial in personal care applications.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. All percentages are in wt. %. All measurements were conducted at 23° C. unless indicated otherwise.

Example 1

Emulsification of 100K PDMS with 949 Emulsion 20 g of 100,000 centistoke (cSt.) Dow Corning® 200 Fluid, a polydimethylsiloxane (PDMS) fluid, was weighed into a Max 40 cup followed by 2.5 g of Dow Corning® 949 Cationic Emulsion, which is an aqueous emulsion containing 35% silicone aminofunctional polymer. The cup was closed and placed inside a DAC-150 SpeedMixer® and the cup was spun at maximum speed (3450 RPM) for 30 seconds. The cup was opened and the walls of the cup were scraped with a spatula and the cup was spun again at maximum speed for 30 seconds. 3 g of 949 Cationic Emulsion was weighed into the cup and the cup was spun for 30 seconds at approximately 2500 RPM. 4.5 g of 949 Cationic Emulsion was added and the cup was again spun for 30 seconds at approximately 2500 RPM. The resulting emulsion consisted of an aqueous oil-in-water (o/w) emulsion of silicone polymer having a total silicone content of approximately 78.3 percent. On a dry basis, this emulsions contained approximately 85 percent PDMS and 15 percent amino-functional PDMS. Particle size of the emulsion was determined using a Malvern Mastersizer® 2000 and Microtrac Nanotrac® and the results were:
Dv50=22.24 µm, Dv90=54.27 µm, Mode 1=0.122 µm, Mode 2=22.24 µm.

Example 2

Emulsification of 600K PDMS with 8170 Microemulsion 43.1 g of 100,000 centistoke (cSt.) Dow Corning® 200 Fluid, a poly(dimethylsiloxane) fluid, was weighed into a Max 40 cup followed by 6.99 g of Dow Corning® CE-8170 AF Microemulsion, which is an aqueous emulsion containing 20% silicone aminofunctional polymer. The cup was closed and placed inside a DAC-150 SpeedMixer® and the cup was spun at maximum speed (3450 RPM) for 30 seconds. The cup was opened and the walls of the cup were scraped with a spatula. The cup was spun again at maximum speed for 30 seconds. 6.59 g of 8170 Cationic Emulsion was weighed into the cup and the cup was spun for 30 seconds at approximately 2500 RPM. The resulting emulsion consisted of an aqueous oil-in-water (o/w) emulsion of silicone polymer having a total silicone content of approximately 80.78 percent. On a dry basis, this emulsions contained approximately 91 percent PDMS and 9 percent amino-functional PDMS. Particle size of the emulsion was determined using a Malvern Mastersizer® 2000 and Microtrac Nanotrac® and the results were as follows:
Dv50=22.894 μm, Dv90=52.195 μm, Mode 1=0.0941 μm, Mode 2=22.984 μm.

Example 3

Emulsification of 100K PDMS with 1785 Emulsion 20 g of 100,000 centistoke (cSt.) Dow Corning® 200 Fluid, a poly(dimethylsiloxane) fluid, was weighed into a Max 40 cup followed by 5 g of Xiameter® MEM 1785 Emulsion which is a 60% aqueous emulsion of high molecular weight OH functional poly(dimethylsiloxane). The cup was closed and placed inside a DAC-150 SpeedMixer® and the cup was spun at maximum speed (3450 RPM) for 30 seconds. The cup was opened and the walls of the cup were scraped with a spatula and the cup was spun again at maximum speed for 30 seconds. 3 g of 1785 Emulsion was weighed into the cup and the cup was spun for 30 seconds at approximately 2500 RPM. 4.5 g of 1785 Emulsion was added and the cup was again spun for 30 seconds at approximately 2500 RPM. The resulting emulsion consisted of an aqueous oil-in-water (o/w) emulsion of silicone polymer having a total silicone content of approximately 86.7 percent. On a dry basis, this emulsions contained approximately 77 percent 100,000 cSt PDMS as large particles and 23 percent high molecular weight, OH functional PDMS as smaller particles. Particle size of the emulsion was determined using a Malvern Mastersizer®. The particle size curve showed two distinct peaks, one centered at 6.5 μm and another that was centered at 35 μm. Particle size as calculated by the instrument was as follows: Dv50=21.66 μm, Dv90=85.31 μm, Mode 1=0.67 μm, Mode 2=33.877 μm.

Example 4

Step-Growth Emulsion Polymerization with 939 Emulsion 20.0 g of a dimethylvinyl-ended polydimethylsiloxane polymer having a kinematic viscosity of approximately 55,000 cSt was weighed into a Max 40 cup followed by 0.41 g of a mixture made by adding 0.729 g of heptamethyltrisiloxane to 24.721 g of a trimethylsiloxy-ended dimethyl-methylhydrogen polysiloxane copolymer having a silicon-bonded hydrogen content of 0.18 percent by weight and having a kinematic viscosity of approximately 10 cSt. This was followed by adding 1 drop from a small pipet (approximately 0.1 g) of Syloff® 4000 Catalyst (Pt catalyst). The cup was closed and the cup was spun in a DAC-150 SpeedMixer® for 20 seconds at maximum speed. 2.0 g of Dow Corning® 939 Cationic Emulsion was added next and the cup was closed and spun for 30 seconds at maximum speed. The walls of the cup were scraped with a spatula and the cup was spun again for 30 seconds at maximum speed. 5.0 g of water was added in 2 equal increments with the cup being spun for 25 seconds at maximum speed after each increment was added. Particle size was measured with a Malvern Mastersizer® 2000 and Microtrac Nanotrac®. Particle size as calculated by the instrument was as follows:
Dv50=13.39 μm, Dv90=25.70 μm, Mode 1=0.301 μm, Mode 2=11.314 μm.

This composition consisted of an approximately 77 percent silicone aqueous emulsion. The silicone phase in this emulsion was made up of approximately 97 percent high viscosity polydimethylsiloxane (large particles) and 3 percent amino-functional polydimethylsiloxane (smaller particles).

Example 5

Step-Growth Emulsion Polymerization with 939 Emulsion 20.0 g of a dimethylvinyl-ended polydimethylsiloxane polymer having a kinematic viscosity of approximately 55,000 cSt was weighed into a Max 40 cup followed by 0.41 g of a mixture made by adding 0.729 g of heptamethyltrisiloxane to 24.721 g of a trimethylsiloxy-ended dimethyl-methylhydrogen polysiloxane copolymer having a silicon-bonded hydrogen content of 0.18 percent by weight and having a kinematic viscosity of approximately 10 cSt. This was followed by adding 1 drop from a small pipet (approximately 0.1 g) of Syloff® 4000 Catalyst (Pt catalyst). The cup was closed and the cup was spun in a DAC-150 SpeedMixer® for 20 seconds at maximum speed. 1.0 g of Dow Corning® 939 Cationic Emulsion was added next and the cup was closed and spun for 30 seconds at maximum speed. Inspection of the contents of the cup revealed that the composition had not inverted. In other words, silicone polymer was the continuous phase. 1.0 g of additional Dow Corning 939 Cationic Emulsion was added and the cup was closed and spun for 30 seconds at maximum speed. The composition in the cup inverted into a water-out emulsion at this stage. The walls of the cup were scraped with a spatula and the cup was spun again for 30 seconds at maximum speed. 8.0 g of Dow Corning® 939 Emulsion was added in 3 equal increments with the cup being spun for 25 seconds at maximum speed after each increment was added. Particle size was measured with a Malvern Mastersizer® 2000 and Microtrac Nanotrac®. Particle size as calculated by the instrument was as follows: Dv50=10.94 μm, Dv90=19.61 μm, Mode 1=0.30 μm, Mode 2=10.41 μm.

This composition consisted of an approximately 78 percent silicone aqueous emulsion. The silicone phase in this emulsion was made up of approximately 85 percent high viscosity polydimethylsiloxane (large particles) and 15 percent amino-functional polydimethylsiloxane (smaller particles).

Example 6

Step-Growth Emulsion Polymerization with 1788 Emulsion 20.0 g of a dimethylvinyl-ended polydimethylsiloxane polymer having a kinematic viscosity of approximately 55,000 cSt was weighed into a Max 40 cup followed by 0.40 g of a mixture made by adding 0.729 g of heptamethyltrisiloxane to 24.721 g of a trimethylsiloxy-ended dimethyl-methylhydrogen polysiloxane copolymer having a silicon-bonded hydrogen content of 0.18 percent by weight and having a kinematic viscosity of approximately 10 cSt. This was followed by adding 1 drop from a small pipet (approximately 0.1 g) of Syloff® 4000 Catalyst (Pt catalyst). The cup was closed and the cup was spun in a DAC-150 SpeedMixer® for 20 seconds at maximum speed. 2.0 g of Dow Corning® 1788 Emulsion (a 49 percent emulsion of high viscosity OH functional polydimethylsiloxane) was added next and the cup was closed and spun for 30 seconds at maximum speed. The walls of the cup were scraped with a spatula and the cup was spun again for 30 seconds at maximum speed. 8.0 g of Dow Corning® 1788 Emulsion was added in 2 equal increments with the cup being spun for 25 seconds at maximum speed after each increment was added. Particle size was measured with a Malvern Mastersizer® 2000 and Microtrac Nanotrac®. Particle size as calculated by the instrument was as follows: Dv50=16.87 µm, Dv90=32.21 µm, Mode 1=0.30 µm, Mode 2=11.01 µm.

This composition consisted of an approximately 83 percent silicone aqueous emulsion. The silicone phase in this emulsion was made up of approximately 81 percent high viscosity polydimethylsiloxane in the form of large particles and 19 percent high viscosity polydimethylsiloxane in the form of smaller particles.

Example 7

Organic Oil with 1785 Silicone Emulsion 20.0 g of Indopol® H-300 polybutene having a kinematic viscosity of 630 cSt (100 C) was weighed into a Max 40 cup followed by 2 g of Xiameter® MEM 1785 Emulsion which is a 60% aqueous emulsion of high molecular weight OH functional polydimethylsiloxane. The cup was closed and placed inside a DAC-150 SpeedMixer® and the cup was spun at maximum speed (3500 RPM) for 30 seconds. The cup was opened and the walls of the cup were scraped with a spatula and the cup was spun again at maximum speed for 30 seconds. 4 g of 1785 Emulsion was weighed into the cup and the cup was spun for 30 seconds at approximately 2500 RPM. Another 4 g of 1785 Emulsion was added and the cup was again spun for 30 seconds at approximately 2500 RPM. The resulting emulsion consisted of an aqueous oil-in-water (o/w) emulsion of polybutene and high viscosity polydimethylsiloxane having a total polymer content of approximately 86.7 percent. On a dry basis, this emulsions contained approximately 77 percent polybutene in larger particles and 23 percent high molecular weight, OH functional PDMS in smaller particles. Particle size of the emulsion was determined using a Malvern Mastersizer® 2000. The particle size curve showed two distinct peaks, one centered at about 0.7 µm and another that was centered at about 10 µm. Particle size as calculated by the instrument was as follows: Dv50=5.57 µm, Dv90=18.02 µm, Mode 1=0.768 µm, Mode 2=11.601 µm.

Example 8

Silicone Oil with Pinesol® Organic Oil Emulsion 20 g of an OH functional polydimethylsiloxane polymer having a viscosity of 50,000 mPa-sec was weighed into a Max 40 cup followed by 0.5 g of Pinesol® Cleaner, which is a microemulsion of 8.7 percent pine oil in water with surfactants and other ingredients. The cup was closed and placed inside a DAC-150 SpeedMixer® and the cup was spun at maximum speed (3450 RPM) for 30 seconds. The cup was opened and the walls of the cup were scraped with a spatula and the cup was spun again at maximum speed for 30 seconds. The resulting emulsion was diluted with additional Pinesol® Cleaner in two 2.5 g increments while the cup was spun for 20 seconds at maximum speed after each dilution. This emulsion contained approximately 80 percent dispersed phase of silicone and pine oil. The dispersed phase was made up of approximately 98 percent silicone polymer and 2 percent pine oil. Particle size of the emulsion was determined using a Malvern Mastersizer® 2000 and Microtrac Nanotrac®. Particle size as calculated by the instrument was as follows: Dv50=3.03 µm, Dv90=4.29 µm, Mode 1=0.102 µm, Mode 2=3.02 µm.

Example 9

Emulsification of 600K PDMS and Joncryl® 77

42.83 g of 600,000 centistoke (cSt.) Dow Corning® 200 Fluid, a polydimethylsiloxane (PDMS) fluid, was weighed into a Max 40 cup followed by 8.60 g of Joncryl® 77, which is an aqueous acrylic emulsion (BASF) having a non-volatile content of 46 wt %. The cup was closed and placed inside a DAC-150 SpeedMixer® and the cup was spun at maximum speed (3450 RPM) for 45 seconds. The cup was opened and the walls of the cup were scraped with a spatula and the cup was spun again at maximum speed for 45 seconds. An additional 8.60 g of Joncryl® 77 Cationic Emulsion was weighed into the cup and the cup was spun for 45 seconds at approximately 3450 RPM. The walls of the cup were scraped with a spatula and the cup was spun again for 45 seconds at approximately 3450 RPM. The resulting emulsion consisted of an aqueous oil-in-water (o/w) bimodal emulsion of the silicone and acrylic polymer having a total silicone and acrylic content of approximately 71 and 13 percent, respectively. On a dry basis, this emulsions contained approximately 84 percent PDMS and 16 percent acrylic polymer. Particle size of the emulsion was determined using a Malvern Mastersizer® and the results were:
Dv50=10.917 µm, Dv90=26.833 µm, Mode 1=0.0751 µm, Mode 2=10.226 µm.

Example 10

Bimodal Emulsion at 88% Si—Emulsification of 600K PDMS With 1785 Emulsion 42.87 g of 600,000 centistoke (cSt.) Dow Corning® 200 Fluid, a poly(dimethylsiloxane) fluid, was weighed into a Max 40 cup followed by 8.55 g of Xiameter® MEM 1785 Emulsion which is a 60% aqueous emulsion of high molecular weight OH functional poly(dimethylsiloxane). The cup was closed and placed inside a DAC-150 SpeedMixer® and the cup was spun at maximum speed (3450 RPM) for 30 seconds. The cup was opened and the walls of the cup were scraped with a spatula and the cup was spun again at maximum speed for 30 seconds. 8.57 g of 1785 Emulsion was weighed into the cup and the cup was spun for 30 seconds at approximately 2500 RPM. The resulting emulsion consisted of an aqueous oil-in-water (o/w) emulsion of silicone polymer having a total silicone content of approximately 88.6 percent. The resulting emulsion was a free flowing opaque material in the dental cup after mixing.

Comparative Example 1

Monomodal Emulsion at 88% Silicone 53.22 g of 100,000 centistoke (cSt.) Dow Corning® 200 Fluid, a poly(dimethylsiloxane) fluid, was weighed into a Max 40 cup followed by 1.2 g of Brij 30, 1.45 g Brij 35 L, and 4.26 g of water (added incrementally). The cup was closed and placed inside a DAC-150 SpeedMixer® and the cup was spun at maximum speed (3450 RPM) for 30 seconds. The cup was opened and the walls of the cup were scraped with a spatula and the cup was spun again at maximum speed for 30 seconds. The resulting emulsion consisted of an aqueous oil-in-water (o/w) emulsion of silicone polymer having a total silicone content of approximately 88 percent. The resulting emulsion was gel-like and formed a solid cone of material in the dental cup after mixing.

The invention claimed is:

1. A process for making a bi-modal emulsion comprising:
   I) forming a mixture comprising
      A) 100 parts by weight of a hydrophobic oil, and
      B) 1 to 1000 part by weight of a water continuous emulsion having at least one surfactant and
   II) admixing additional quantities of the water continuous emulsion and/or water to the mixture from step I) to form a bi-modal emulsion, wherein the water continuous emulsion is a silicone emulsion and the bi-modal emulsion contains less than 1 weight cyclosiloxanes.

2. The process of claim 1 wherein the mixture of step I) consists essentially of components A) and B).

3. The process of claim 1 wherein the additional quantities of the water continuous emulsion and/or water added in step II to the mixture from step I is done in incremental portions, whereby each incremental portion comprises less than 50 weight % of the mixture from step I and each incremental portion of water continuous emulsion is added successively to the previous after the dispersion of the previous incremental portion of water continuous emulsion and/or water, wherein sufficient incremental portions of water continuous emulsion and/or water are added to form the bi-modal emulsion.

4. The process of claim 1 wherein the hydrophobic oil is a silicone.

5. The process of claim 1 wherein the hydrophobic oil is an organic oil.

6. The process of claim 1 where the quantity of the water continuous emulsion and/or water added to the mixture provides a bi-modal emulsion containing at least 75% by weight of components A) and B).

7. The process of claim 1 where the bi-modal emulsion has a viscosity less than 100,000 cP.

8. The process of claim 1 where the surfactant concentration in the bi-modal emulsion is less than 1 weight %.

9. The bi-modal emulsion produced by claim 1.

10. The process of claim 4 where the bi-modal emulsion has a viscosity less than 100,000 cP.

11. The process of claim 3 wherein the hydrophobic oil is a silicone.

12. A process for making a bi-modal emulsion comprising:
    I) forming a mixture comprising
       A) 100 parts by weight of a hydrophobic oil, and
       B) 1 to 1000 part by weight of a water continuous emulsion having at least one surfactant and
    II) admixing additional quantities of the water continuous emulsion and/or water to the mixture from step I) to form a bi-modal emulsion, wherein the hydrophobic oil is a silicone and the bi-modal emulsion contains less than 1 weight % cyclosiloxanes.

13. The process of claim 12 wherein the water continuous emulsion is a silicone emulsion.

14. The process of claim 12 wherein the water continuous emulsion is an organic emulsion.

15. The process of claim 12 where the bi-modal emulsion has a viscosity less than 100,000 cP.

16. The process of claim 12 where the quantity of the water continuous emulsion and/or water added to the mixture provides a bi-modal emulsion containing at least 75% by weight of components A) and B).

* * * * *